(12) United States Patent
Hatlestad et al.

(10) Patent No.: US 8,200,326 B2
(45) Date of Patent: Jun. 12, 2012

(54) CALIBRATION OF IMPEDANCE MONITORING OF RESPIRATORY VOLUMES USING THORACIC D.C. IMPEDANCE

(75) Inventors: John D. Hatlestad, Maplewood, MN (US); Loell Boyce Moon, Ham Lake, MN (US); Jesse W. Hartley, Lino Lakes, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 352 days.

(21) Appl. No.: 12/557,372

(22) Filed: Sep. 10, 2009

(65) Prior Publication Data

US 2009/0326599 A1  Dec. 31, 2009

Related U.S. Application Data

(62) Division of application No. 11/114,661, filed on Apr. 26, 2005, now Pat. No. 7,603,170.

(51) Int. Cl.
*A61B 5/05* (2006.01)
*A61B 5/08* (2006.01)

(52) U.S. Cl. ........................................ 600/547; 600/529

(58) Field of Classification Search .................. 600/538, 600/547; 607/17, 20
See application file for complete search history.

(56) References Cited

U.S. PATENT DOCUMENTS

| | | | |
|---|---|---|---|
| 3,340,867 A | 9/1967 | Kubicek et al. | |
| 3,608,542 A | 9/1971 | Pacela et al. | |
| 3,871,359 A | 3/1975 | Pacela | |
| 4,003,379 A | 1/1977 | Ellinwood, Jr. | |
| 4,059,169 A | 11/1977 | Hagen | |
| RE30,101 E | 9/1979 | Kubicek et al. | |
| 4,271,192 A | 6/1981 | Wurtman et al. | |
| 4,437,469 A | 3/1984 | Djordjevich et al. | |
| 4,450,527 A | 5/1984 | Sramek | |
| 4,470,987 A | 9/1984 | Wurtman et al. | |
| 4,472,420 A | 9/1984 | Toth | |
| 4,472,431 A | 9/1984 | Toth | |
| 4,559,946 A | 12/1985 | Mower | |
| 4,567,892 A | 2/1986 | Plicchi et al. | |
| 4,576,183 A | 3/1986 | Plicchi et al. | |

(Continued)

FOREIGN PATENT DOCUMENTS

EP  348271 A1  12/1989

(Continued)

OTHER PUBLICATIONS

"U.S. Appl. No. 10/267,982, Supplemental Amendment filed Jan. 18, 2006", 12 pgs.

(Continued)

*Primary Examiner* — Patricia Mallari
*Assistant Examiner* — Christian Jang
(74) *Attorney, Agent, or Firm* — Schwegman, Lundberg & Woessner, P.A.

(57) ABSTRACT

A system includes an implantable medical device that includes a trans-thoracic impedance measurement circuit providing a trans-thoracic impedance signal of a subject. A controller is coupled to the trans-thoracic impedance circuit. The controller extracts a respiration signal from the trans-thoracic impedance signal, measures a breathing volume of the subject using the amplitude of the respiration signal and a breathing volume calibration factor, computes an adjusted breathing volume calibration factor using a reference baseline value of the trans-thoracic impedance and a measured baseline value of the trans-thoracic impedance, and computes a calibrated breathing volume using the adjusted breathing volume calibration factor.

22 Claims, 5 Drawing Sheets

U.S. PATENT DOCUMENTS

| | | | |
|---|---|---|---|
| 4,651,716 A | 3/1987 | Forester et al. | |
| 4,686,987 A | 8/1987 | Salo et al. | |
| 4,693,253 A | 9/1987 | Adams | |
| 4,880,005 A | 11/1989 | Pless et al. | |
| 4,884,576 A | 12/1989 | Alt | |
| 4,904,472 A | 2/1990 | Belardinelli et al. | |
| 4,919,136 A | 4/1990 | Alt | |
| 4,980,379 A | 12/1990 | Belardinelli et al. | |
| 4,987,897 A | 1/1991 | Funke | |
| 5,002,052 A | 3/1991 | Haluska | |
| 5,003,976 A | 4/1991 | Alt | |
| 5,025,786 A | 6/1991 | Siegel | |
| 5,031,629 A | 7/1991 | DeMarzo | |
| 5,036,849 A | 8/1991 | Hauck et al. | |
| 5,113,869 A | 5/1992 | Nappholz et al. | |
| 5,117,825 A | 6/1992 | Grevious | |
| 5,178,154 A | 1/1993 | Ackmann et al. | |
| 5,179,947 A | 1/1993 | Meyerson et al. | |
| 5,199,428 A | 4/1993 | Obel et al. | |
| 5,213,098 A | 5/1993 | Bennett et al. | |
| 5,215,083 A | 6/1993 | Drane et al. | |
| 5,233,985 A | 8/1993 | Hudrlik | |
| 5,246,008 A | 9/1993 | Mueller | |
| 5,271,395 A | 12/1993 | Wahlstrand et al. | |
| 5,273,034 A | 12/1993 | Nilsson | |
| 5,282,836 A | 2/1994 | Kreyenhagen et al. | |
| 5,282,840 A | 2/1994 | Hudrlik | |
| 5,284,136 A | 2/1994 | Hauck et al. | |
| 5,292,343 A | 3/1994 | Blanchette et al. | |
| 5,300,093 A | 4/1994 | Koestner et al. | |
| 5,309,917 A | 5/1994 | Wang et al. | |
| 5,313,953 A | 5/1994 | Yomtov et al. | |
| 5,324,309 A | 6/1994 | Kallok | |
| 5,324,315 A | 6/1994 | Grevious | |
| 5,344,429 A | 9/1994 | Smits | |
| 5,354,317 A | 10/1994 | Alt | |
| 5,354,319 A | 10/1994 | Wyborny et al. | |
| 5,355,894 A | 10/1994 | Sivard | |
| 5,366,485 A | 11/1994 | Kroll et al. | |
| 5,370,665 A | 12/1994 | Hudrlik | |
| 5,391,190 A | 2/1995 | Pederson et al. | |
| 5,404,877 A | 4/1995 | Nolan et al. | |
| 5,405,362 A | 4/1995 | Kramer et al. | |
| 5,411,031 A | 5/1995 | Yomtov | |
| 5,431,682 A | 7/1995 | Hedberg | |
| 5,441,525 A | 8/1995 | Shelton et al. | |
| 5,443,073 A | 8/1995 | Wang et al. | |
| 5,454,377 A | 10/1995 | Dzwonczyk et al. | |
| 5,464,434 A | 11/1995 | Alt | |
| 5,479,369 A | 12/1995 | Matsumura et al. | |
| 5,501,701 A | 3/1996 | Markowitz et al. | |
| 5,505,209 A | 4/1996 | Reining | |
| 5,507,785 A | 4/1996 | Deno | |
| 5,522,860 A | 6/1996 | Molin et al. | |
| 5,526,808 A | 6/1996 | Kaminsky | |
| 5,534,018 A | 7/1996 | Wahlstrand et al. | |
| 5,540,728 A | 7/1996 | Shelton et al. | |
| 5,562,711 A | 10/1996 | Yerich et al. | |
| 5,562,712 A | 10/1996 | Steinhaus et al. | |
| 5,626,623 A | 5/1997 | Kieval et al. | |
| 5,642,734 A | 7/1997 | Ruben et al. | |
| 5,676,686 A | 10/1997 | Jensen et al. | |
| 5,685,316 A | 11/1997 | Schookin et al. | |
| 5,706,829 A | 1/1998 | Kadri | |
| 5,722,999 A | 3/1998 | Snell | |
| 5,725,561 A | 3/1998 | Stroebel et al. | |
| 5,725,562 A | 3/1998 | Sheldon | |
| 5,732,710 A | 3/1998 | Rabinovich et al. | |
| 5,735,284 A | 4/1998 | Tsoglin et al. | |
| 5,749,369 A | 5/1998 | Rabinovich et al. | |
| 5,749,900 A | 5/1998 | Schroeppel et al. | |
| 5,782,774 A | 7/1998 | Shmulewitz | |
| 5,782,879 A | 7/1998 | Rosborough et al. | |
| 5,782,884 A | 7/1998 | Stotts et al. | |
| 5,788,643 A | 8/1998 | Feldman | |
| 5,791,349 A | 8/1998 | Shmulewitz | |
| 5,800,464 A | 9/1998 | Kieval | |
| 5,824,029 A | 10/1998 | Weijand et al. | |
| 5,865,760 A | 2/1999 | Lidman et al. | |
| 5,874,420 A | 2/1999 | Pelleg | |
| 5,876,353 A | 3/1999 | Riff | |
| 5,882,352 A | 3/1999 | Duncan et al. | |
| 5,913,879 A | 6/1999 | Ferek-Petric et al. | |
| 5,919,210 A | 7/1999 | Lurie et al. | |
| 5,957,861 A | 9/1999 | Combs et al. | |
| 5,957,957 A | 9/1999 | Sheldon | |
| 5,974,340 A | 10/1999 | Kadhiresan | |
| 5,978,705 A | 11/1999 | KenKnight et al. | |
| 6,026,324 A | 2/2000 | Carlson | |
| 6,035,233 A | 3/2000 | Schroeppel et al. | |
| 6,044,297 A | 3/2000 | Sheldon et al. | |
| 6,049,735 A | 4/2000 | Hartley et al. | |
| 6,075,015 A | 6/2000 | Sestelo et al. | |
| 6,076,015 A | 6/2000 | Hartley et al. | |
| 6,078,834 A | 6/2000 | Lurie et al. | |
| 6,095,987 A | 8/2000 | Shmulewitz et al. | |
| 6,104,949 A | 8/2000 | Pitts et al. | |
| 6,154,672 A | 11/2000 | Pendekanti et al. | |
| 6,161,038 A | 12/2000 | Schookin et al. | |
| 6,186,955 B1 | 2/2001 | Baura | |
| 6,224,907 B1 | 5/2001 | Davar et al. | |
| 6,228,033 B1 | 5/2001 | Koobi et al. | |
| 6,266,565 B1 | 7/2001 | Er et al. | |
| 6,292,689 B1 | 9/2001 | Wallace et al. | |
| 6,298,267 B1 | 10/2001 | Rosborough et al. | |
| 6,314,322 B1 | 11/2001 | Rosenberg | |
| 6,317,631 B1 | 11/2001 | Ben-Haim et al. | |
| 6,336,903 B1 | 1/2002 | Bardy | |
| 6,409,675 B1 | 6/2002 | Turcott | |
| 6,411,844 B1 | 6/2002 | Steve et al. | |
| 6,438,408 B1 | 8/2002 | Mulligan et al. | |
| 6,473,640 B1 | 10/2002 | Erlebacher | |
| 6,511,438 B2 | 1/2003 | Bernstein et al. | |
| 6,512,949 B1 | 1/2003 | Combs et al. | |
| 6,560,481 B1 | 5/2003 | Heethaar et al. | |
| 6,561,986 B2 | 5/2003 | Baura et al. | |
| 6,574,506 B2 | 6/2003 | Kramer et al. | |
| 6,595,927 B2 | 7/2003 | Pitts-Crick et al. | |
| 6,600,949 B1 | 7/2003 | Turcott | |
| 6,602,201 B1 | 8/2003 | Hepp | |
| 6,625,492 B2 | 9/2003 | Florio et al. | |
| 6,636,754 B1 | 10/2003 | Baura et al. | |
| 6,643,543 B2 | 11/2003 | Takehara et al. | |
| 6,665,564 B2 | 12/2003 | Lincoln et al. | |
| 6,678,547 B2 | 1/2004 | Carlson et al. | |
| 6,714,813 B2 | 3/2004 | Ishigooka et al. | |
| 6,748,271 B2 | 6/2004 | Spinelli et al. | |
| 6,752,765 B1 | 6/2004 | Jensen et al. | |
| 6,795,733 B1 | 9/2004 | Lu | |
| 6,811,537 B2 | 11/2004 | Bardy | |
| 6,829,503 B2 | 12/2004 | Alt | |
| 6,907,288 B2 | 6/2005 | Daum | |
| 6,908,437 B2 | 6/2005 | Bardy | |
| 6,912,420 B2 | 6/2005 | Scheiner et al. | |
| 7,003,346 B2 | 2/2006 | Singer | |
| 7,149,573 B2 | 12/2006 | Wang | |
| 7,177,681 B2 | 2/2007 | Zhu et al. | |
| 7,191,000 B2 | 3/2007 | Qingsheng et al. | |
| 7,333,854 B1 | 2/2008 | Brewer et al. | |
| 7,340,296 B2 | 3/2008 | Stahmann et al. | |
| 7,387,610 B2 | 6/2008 | Stahmann et al. | |
| 7,422,560 B2 | 9/2008 | Hatlestsad et al. | |
| 7,603,170 B2 | 10/2009 | Maplewood et al. | |
| 7,672,718 B2 | 3/2010 | Stahmann et al. | |
| 7,881,781 B2 | 2/2011 | Stahmann et al. | |
| 2001/0020138 A1 | 9/2001 | Ishigooka et al. | |
| 2001/0025137 A1 | 9/2001 | Webb et al. | |
| 2002/0115939 A1 | 8/2002 | Mulligan et al. | |
| 2002/0123674 A1 | 9/2002 | Plicchi et al. | |
| 2002/0138014 A1 | 9/2002 | Baura et al. | |
| 2002/0147475 A1 | 10/2002 | Scheiner et al. | |
| 2002/0147476 A1 | 10/2002 | Daum | |
| 2002/0193689 A1 | 12/2002 | Bernstein et al. | |
| 2003/0023279 A1 | 1/2003 | Spinelli et al. | |
| 2003/0028221 A1 | 2/2003 | Zhu et al. | |
| 2003/0055461 A1 | 3/2003 | Girouard et al. | |
| 2003/0074029 A1 | 4/2003 | Deno et al. | |

| 2003/0105496 | A1 | 6/2003 | Yu et al. |
| 2003/0176896 | A1 | 9/2003 | Lincoln et al. |
| 2003/0191503 | A1 | 10/2003 | Zhu et al. |
| 2003/0220580 | A1 | 11/2003 | Alt |
| 2004/0049235 | A1 | 3/2004 | Deno et al. |
| 2004/0073128 | A1 | 4/2004 | Hatlestad et al. |
| 2004/0086864 | A1 | 5/2004 | Lo et al. |
| 2004/0102712 | A1 | 5/2004 | Belalcazar et al. |
| 2004/0116819 | A1 | 6/2004 | Alt |
| 2004/0127807 | A1 | 7/2004 | Hatlesad et al. |
| 2004/0133079 | A1 | 7/2004 | Mazar et al. |
| 2004/0147982 | A1 | 7/2004 | Bardy |
| 2004/0172080 | A1 | 9/2004 | Stadler et al. |
| 2004/0215097 | A1 | 10/2004 | Wang |
| 2004/0215270 | A1 | 10/2004 | Ritscher et al. |
| 2005/0004609 | A1 | 1/2005 | Stahmann et al. |
| 2005/0021098 | A1 | 1/2005 | Spinelli et al. |
| 2005/0080460 | A1 | 4/2005 | Wang et al. |
| 2005/0119586 | A1 | 6/2005 | Coyle et al. |
| 2005/0124908 | A1 | 6/2005 | Belalcazar et al. |
| 2005/0137480 | A1 | 6/2005 | Alt et al. |
| 2005/0177062 | A1 | 8/2005 | Skrabal et al. |
| 2005/0283197 | A1 | 12/2005 | Daum et al. |
| 2006/0020295 | A1 | 1/2006 | Brockway et al. |
| 2006/0041280 | A1 | 2/2006 | Stahmann et al. |
| 2006/0135886 | A1 | 6/2006 | Lippert et al. |
| 2006/0241512 | A1 | 10/2006 | Kwok et al. |
| 2006/0241513 | A1 | 10/2006 | Hatlestad et al. |
| 2006/0258952 | A1 | 11/2006 | Stahmann et al. |
| 2006/0264776 | A1 | 11/2006 | Stahmann et al. |
| 2006/0293609 | A1 | 12/2006 | Stahmann et al. |
| 2008/0082001 | A1 | 4/2008 | Hatlestad et al. |
| 2008/0108907 | A1 | 5/2008 | Stahmann et al. |
| 2009/0005697 | A1 | 1/2009 | Hatlestsad et al. |
| 2010/0076336 | A1 | 3/2010 | Stahmann |

FOREIGN PATENT DOCUMENTS

| EP | 0584388 A1 | 3/1994 |
| EP | 0620420 A1 | 10/1994 |
| EP | 0663219 A1 | 7/1995 |
| EP | 1057498 A2 | 12/2000 |
| EP | 1078597 A2 | 2/2001 |
| EP | 606301 B1 | 12/2001 |
| EP | 1247487 A1 | 10/2002 |
| EP | 1275342 A2 | 1/2003 |
| EP | 771172 B1 | 4/2003 |
| WO | WO-84/00227 A1 | 1/1984 |
| WO | WO-93/04627 A1 | 3/1993 |
| WO | WO-96/01586 A1 | 1/1996 |
| WO | WO-97/37591 A1 | 10/1997 |
| WO | WO-97/38628 A1 | 10/1997 |
| WO | WO-98/51211 A1 | 11/1998 |
| WO | WO-01/41638 A1 | 6/2001 |
| WO | WO-02/053026 A2 | 7/2002 |
| WO | WO-02/053228 A1 | 7/2002 |
| WO | WO-03/020364 A2 | 3/2003 |

OTHER PUBLICATIONS

"U.S. Appl. No. 10/267,982, Supplemental Amendment filed Aug. 29, 2006", 13 pgs.

"U.S. Appl. No. 10/921,503, Amendment and Response filed Oct. 12, 2007 to Non-Final Office Action mailed Jul. 13, 2007", 21 pgs.

"U.S. Appl. No. 10/921,503, Notice of Allowance mailed Jan. 31, 2008", 8 pgs.

"U.S. Appl. No. 10/921,503, Response to Restriction Requirement and Preliminary Amendment filed Apr. 9, 2007", 19 pgs.

"U.S. Appl. No. 10/921,503, Restriction Requirement mailed Mar. 7, 2007", 6 pgs.

"U.S. Appl. No. 10/921,503, Supplemental Amendment and Response filed Oct. 25, 2007 to Office Action mailed Jul. 13, 2007", 24 pgs.

"U.S. Appl. No. 10/921,503, Non-Final Office Action mailed Jul. 13, 2007", 5 pgs.

"U.S. Appl. No. 11/114,661, Restriction Requirement mailed Mar. 31, 2008", 9 pgs.

"U.S. Appl. No. 11/114,661, Non-Final Office Action mailed Jun. 13, 2008", 7 pgs.

"U.S. Appl. No. 11/114,661, Response filed Sep. 15, 2008 to Non-Final Office Action mailed Jun. 13, 2008", 12 pgs.

"U.S. Appl. No. 11/114,661, Final Office Action mailed Mar. 3, 2009", 9 pgs.

"U.S. Appl. No. 11/114,661, Notice of Allowance mailed Jun. 1, 2009", 6 pgs.

"U.S. Appl. No. 11/114,661, Response filed May 4, 2009 to Final Office Action mailed Mar. 3, 2009", 9 pgs.

"U.S. Appl. No. 11/126,689, Advisory Action mailed Aug. 27, 2007", 3 pgs.

"U.S. Appl. No. 11/126,689, Final Office Action mailed Jun. 14, 2007", 13 pgs.

"U.S. Appl. No. 11/126,689, Non-Final Office Action mailed Jan. 3, 2007", 9 pgs.

"U.S. Appl. No. 11/126,689, Non-Final Office Action mailed Feb. 6, 2009", 14 pgs.

"U.S. Appl. No. 11/126,689, Non-Final Office Action mailed Jul. 21, 2008", 6 pgs.

"U.S. Appl. No. 11/126,689, Non-Final Office Action mailed Oct. 19, 2007", 11 pgs.

"U.S. Appl. No. 11/126,689, Response and Preliminary Amendment filed Oct. 10, 2006 to Restriction Requirement mailed Sep. 8, 2006", 12 pgs.

"U.S. Appl. No. 11/126,689, Response filed Jan. 22, 2008 to Non-Final Office Action mailed Oct. 19, 2007", 23 pgs.

"U.S. Appl. No. 11/126,689, Response filed Apr. 3, 2007 to Non-Final Office Action mailed Jan. 3, 2007", 22 pgs.

"U.S. Appl. No. 11/126,689, Response filed Aug. 14, 2007 to Final Office Action mailed Jun. 14, 2007", 13 pgs.

"U.S. Appl. No. 11/126,689, Response filed Oct. 21, 2008 to Non Final Office Action mailed Jul. 21, 2008", 13 pgs.

"U.S. Appl. No. 11/126,689, Response filed Jun. 10, 2009 to Non Final Office Action mailed Feb. 6, 2009", 18 pgs.

"U.S. Appl. No. 11/126,689, Restriction Requirement mailed Sep. 8, 2006", 5 pgs.

"U.S. Appl. No. 11/132,109, Decision from Pre-Appeal Brief Review mailed Aug. 9, 2007", 2 pgs.

"U.S. Appl. No. 11/132,109, Final Office Action mailed Jan. 22, 2007", 13 pgs.

"U.S. Appl. No. 11/132,109, Non-Final Office Action Mailed Jul. 7, 2006", 10 pgs.

"U.S. Appl. No. 11/132,109, Notice of Allowance mailed Oct. 5, 2007", 10 pgs.

"U.S. Appl. No. 11/132,109, Pre-Appeal Brief Request for Review filed Apr. 23, 2007", 5 pgs.

"U.S. Appl. No. 11/132,109, Response filed Oct. 10, 2006 to Non-Final Office Action mailed Jul. 7, 2006", 20 pgs.

"U.S. Appl. No. 11/972,405, Non-Final Office Action mailed Jun. 12, 2009", 9 pgs.

"U.S. Appl. No. 12/139,948 Non-Final Office Action mailed Feb. 6, 2009", 6 pgs.

"U.S. Appl. No. 12/139,948, Notice of Allowance mailed Sep. 4, 2009", 6 pgs.

"U.S. Appl. No. 12/139,948, Response filed Apr. 27, 2009 to Non Final Office Action mailed Feb. 6, 2009", 8 pgs.

"U.S. Appl. No. 12/628,384, Non-Final Office Action mailed Apr. 6, 2010", 5 pgs.

"U.S. Appl. No. 12/628,384, Notice of Allowance mailed Sep. 28, 2010", 7 pgs.

"U.S. Appl. No. 12/628,384, Response filed Jul. 9, 2010 to Non Final Office Action mailed Apr. 6, 2010", 12 pgs.

"Heart Sounds", [online]. [retrieved on Dec. 8, 2005]. Retrieved from the Internet: <URL: http://www.chfpatients.com/faq/s3s4.htm>, 4 pgs.

"Medtronic Announces European Release of Innovative InSync Sentry™ Cardiac Resynchronization Therapy Defibrillator", [online]. [retrieved Nov. 23, 2005]. Retrieved from the Internet: <URL: http://www.medtronic.com/newsroom/news_20040614a.html>, (2004), 2 pgs.

"Medtronic: InSync™ Sentry 7298: Dual Chamber Implantable Cardioverter Defibrillator with Cardiac Resynchronization Therapy (VVE-DDR) and Opti-Vol™ Fluid Monitoring: Reference Manual", (2004), 420 pgs.

Adamicza, A., et al., "Changes in transthoracic electrical impedance during endotoxemia in dogs", *Acta Physiol Hung.*, 85(4), (1997-98), 291-302.

Adamicza, A., et al., "Investigation of the thoracic electrical impedance during endotoxemia in dogs", *Acta Chir Hung.*, 36(1-4), 1997, 1-3.

Alt, E., et al., "Control of Pacemaker Rate by Impedance-based Respiratory Minute Ventilation", Chest, 92(2), (Aug. 1987), 247-252.

Baarends, E. M., et al., "Body-water compartments measured by bio-electrical impedance spectroscopy in patients with chronic obstructive pulmonary disease", *Clinical Nutrition*, 17(1), (Feb. 1998), 15-22.

Belalcazar, A., et al., "Improved lung edema monitoring with coronary vein pacing leads", *Pacing and Clinical Electrophysiology*, 26(4 pt. II), (Abstract 18), (Apr. 2003), p. 933.

Belalcazar, A., et al., "Improved lung edema monitoring with coronary vein pacing leads: a simulation study", *Physiological Measurement*, vol. 25, (2004), 475-487.

Berman, Irwin R, et al., "Transthoracic electrical impedance s a guide to intravascular overload", *Archives of Surgery*, 102(1), (Jan. 1971), 61-64.

Bradbury, M. G., et al., "Assessment of the sensitivity of bioimpedance to volume changes in body water", *Pediatr Nephrol.*, 9(3), (Jun. 1995), 337-340.

Bussmann, W. D., et al., "Effect of Nitroglycerin Sublingualiy in the Emergency Management of "Classical" Pulmonary Oedema.", *Deutsche medizinische Wochenschrift*, 102(10), (1946), 9 pgs.

Campbell, J. H, et al., "Clinical applications of electrical impedance tomography in the monitoring of changes in intrathoracic fluid volumes", *Physiol. Meas.*, vol. 15, (1994), A217-A222.

Campbell, J. H, et al., "Detection of changes in intrathoracic fluid in man using electrical impedance tomography", *Clinical Science*, vol. 87, (1994), 97-101.

Charach, G., et al., "Transthoracic monitoring of the impedance of the right lung in patients with cardiogenic pulmonary edema", *Critical Care Medicine*, 29(6), (Jun. 2001), 1137-1144.

Chiolero, R. L., et al., "Assessment of changes in body water by bioimpedance in acutely ill surgical patients", *Intensive Care Medicine*, 18(6), (1992), 322-326.

Defaye, P., et al., "Automatic Recognition of Abnormal Respiratory Events During Sleep by a Pacemaker Transthoracic Impedance Sensor", *Journal of Cardiovascular Electrophysiology*, 15(9), (Sep. 2004), 1034-40.

Denniston, J. C, et al., "Factors Influencing the measurement of stroke volume by electrical impedance", Physiology (1372-1377), (Abstract No. 1373), p. 463, (1975).

Denniston, J. C., et al., "Measurement of pleural effusion by electrical impedance", Journal of Applied Physiology, 38(5), (May 1975), 851-857.

Ebert, T J, et al., "The use of thoracic impedance for determining thoracic blood volume changes in man", *Aviat Space Environ Med.*, 57(1), (Jan. 1986), 49-53.

Ellenbogen, K. A., et al., "Rate-adaptive pacing based on impedance-derived minute ventilation", *Clinical Cardiac Pacing*, Philadelphia : Saunders, (1995), 219-233.

Ellenbogen, K. A., et al., "The Electrode-Tissue Interface and the Foreign Body Response", *Clinical Cardiac Pacing*, Philadelphia : Saunders, (1995), 22-23.

Fein, A., et al., "Evaluation of Transthoracic Electrical Impedance in the Diagnosis of Pulmonary Edema", *Circulation*, 60(5), (Nov. 1979), 1156-1160.

Fleischhauer, J., et al., "Electrical resistances of interstitial and microvascular space as determinants of the extracellular electrical field and velocity of propagation in ventricular myocardium", *Circulation*, 92(3), (Aug. 1, 1995), 587-594.

Foreman, B, et al., "Intra-thoracic impedance: a surrogate measure of thoracic fluid—fluid accumulation status trial (FAST)", *Journal of Cardiac Failure*, 10(4 Suppl), (Abstract 251), (2004), p. S86.

Forro, M., et al., "Total body water and ECFV measured using bioelectrical impedance analysis and indicator dilution in horses", *Journal of Applied Physiology*, 89(2), (Aug. 2000), 663-671.

Frerichs, I., et al., "Electrical impedance tomography in monitoring experimental lung injury", *Intensive Care Med.*, 24(8), (Aug. 1998), 829-836.

Garland, J. S., et al., "Measurement of extravascular lung water in hemodialysis patients using blood ultrasound velocity and optical density dilution.", *ASAIO Journal* 2002 48(4), (Jul.-Aug. 2002), 398-403.

Goovaerts, H. G, et al., "Microprocessor-based system for measurement of electrical impedances during haemodialysis and in postoperative care", *Medical & Biological Engineering Computing*, vol. 26, (Jan. 1988), 78-80.

Gotshall, R W, et al., "Bioelectric impedance as an index of thoracic fluid.", Aviation Space and Environmental Medicine, 70(1), (Jan. 1999), 58-61.

Grimbert, F., et al., "Pulmonary water and thoracic impedance. Evaluation of a measurement technic]", *Annales de L'anesthésiologie Française*, 16 Spec No. 2-3, (French, w/ English Abstract), (1975), 157-163.

Harris, N. D., et al., "Applications of applied potential tomography (APT) in respiratory medicine", *Clinical Physics and Physiological Measurement*, 8 Suppl A, (1987), 155-65.

Hoon, R. S., et al., "Changes in Transthoracic electrical impedance at high altitude", *British Heart Journal*, vol. 39, (1977), 61-66.

Hull, E. T, et al., "The Transthoracic Impedance Method for the Determination of the Degree and Change in Extravascular Water", *Acta Tuberc. Pneumol. Belg.*, 68(4), (1977), 369-377.

Hull, E. T, et al., "Transthoracic electrical impedance: artifacts associated with electrode movement", *Resuscitation*, 6(2), (1978), 115-124.

Ishibe, Y., et al., "Transthoracic electrical impedance method for measurement of pulmonary edema in vivo", *Masui*; 27(13), Japanese, (w/ English Abstract), (Dec. 1978), 1559-1567.

Joekes, A. M., et al., "Impedance Cardiography—Its value in an intensive care unit", D) *Materiels et techniques/Cardiocirculatory Equipment and Technics*, (Abstract No. 141), 1 pg, (1977).

Keller, G., et al., "Monitoring of Pulmonary Fluid Volume and Stroke Volume by Impedance Cardiography in Patients on Hemodialysis", *Chest*, 72(1), (Jul. 1977), 56-62.

Khan, M. R, et al., "Quantitative electrical-impedance plethysmography for pulmonary oedema", *Medical & Biological Engineering & Computing*, vol. 15, Nov. 1977), 627-633.

Kiesler, T. W., et al., "Impedance cardiography by use of a spot-electrode array to track changes in cardiac output in anesthetized dogs.", *Journal of the American Veterinary Medical Association*, 196(11), (Jun. 1, 1990), 1804-1810.

Koizumi, T., "Changes of transthoracic impedance (zinf 0 and deltaz) in newborn infants", *Acta Neonatol. Jpn.*, 14(3), (w/ English Abstract), (1978), 335-340.

Kunst, P. W., et al., "Electrical impedance tomography in the assessment of extravascular lung water in noncardiogenic acute respiratory failure", *Chest*, 116(6), (Dec. 1999), 1695-1702.

Kurimoto, et al., "A Case of Pulmonary Edema in a Horse Treated for Cardiac Ailments", *J. Equine Sci*, vol. 13 No. 1., (2002), 29-34.

Kusumoto, F. M., et al., "Medical Progress: Cardiac Pacing", New England Journal of Medicine, 334(2), (Jan. 11, 1996), 89-98.

Larsen, F., et al., "Influence of furosemide and body posture on transthoracic electrical impedance in AMI", *Chest*, 90(5), (Nov. 1986), 733-737.

Laszlo, Z., et al., "Cardiovascular and Hormonal Changes with Different Angles of Head-up Tilt in Men", Physiol. Res. vol. 50, (2001), 71-82.

Lau, C P, et al., "Rate-responsive pacing with a pacemaker that detects respiratory rate (Biorate): clinical advantages and complications", *Clinical Cardiology*, 11(5), (May 1988), 318-324.

Lau, C. P., "The range of sensors and algorithms used in rate adaptive cardiac pacing", *Pacing and clinical electrophysiology: PACE*, 15(8), (Aug. 1992), 1177-1211.

Leung, Zoe KC, et al., "Feasibility of an automatic atrial and ventricular threshold determination using thransthoracic using impedance", *Pacing and Clinical Electrophysiology*, vol. 19, Part II, (Abstract 263), (Apr. 1996), p. 631.

Luepker, R. V., et al., "Transthoracic Electrical Impedance: Quantitative Evaluation of a Non-Invasive Measure of Thoracic Fluid Volume", *American Heart Journal*, 85(1), (Jan. 1973), 83-93.
Mai, J., et al., "Enhanced Rate Response Algorithm for Orthostatic Compensation Pacing", *Pacing Clin Electrophysiol, 23, Naspe Abstracts*, (Abstract No. 678), (Apr. 2000), p. 722.
McCarty, R. N, et al., "Assessment of pulmonary edema in acute congestive heart failure with impedance cardiography", *J Am Osteopath Assoc.*, 74(9), (May 1975), p. 879.
McNamee, J. E., et al., "Peribronchial electrical admittance measures lung edema and congestion in the dog", *Special Communications, Electrical Admittance and Pulmonary Edema*, 337-341.
Newell, J. C., et al., "Assessment of acute pulmonary edema in dogs by electrical impedance imaging", *IEEE Transactions on Biomedical Engineering*, 43(2), (Feb. 1996), 133-138.
Nierman, D. M., et al., "Evaluation of transthoracic bioelectrical impedance analysis in monitoring lung water during diuresis", *Applied Cardiopulmonary Pathophysiology*, 7(1), (1997), 57-62.
Nierman, David M, "Transthoracic Bioimpedance Can Measure Extravascular Lung Water in Acute Lung Injury1", *Journal of Surgical Research 65*, Article No. 0350, (1996), 101-108.
Noble, T. J., et al., "Diuretic induced change in lung water assessed by electrical impedance tomography", *Physiol Meas.*, 21(1), (Feb. 2000), 155-63.
Nukiwa, T., et al., "Responses of Serum and Lung Angiotensin-Converting Enzyme Activities in the Early Phase of Pulmonary Damage Induced by Oleic Acid in Dogs", *Am Rev Respir Dis.*, 126(6), (Dec. 1982), 1080-1086.
Petersen, J. R..., et al., "Electrical impedance measured changes in thoracic fluid content during thoracentesis", *Clin Physiol.*, 14(4), (Jul. 1994), 459-466.
Petersen, M. E., et al., "Cardiac pacing for vasovagal syncope: a reasonable therapeutic option?", *Pacing Clin Electrophysiol.*, 20(3 Pt 2), (Mar. 1997), 824-826.
Platia, E. V., et al., "Time Course of Transvenous Pacemaker Stimulation Impedance, Capture Threshold, and Electrogram Amplitude", *Pacing Clin Electrophysiol.*, 9(5), (Sep./Oct. 19), 620-625, (1986).
Pomerantz, M, et al., "Transthoracic electrical impedance for the early detection of pulmonary edema", *Surgery*, 66(1), (Jul. 1969), 260-268.
Raaijmakers, E., et al., "Estimation of non-cardiogenic pulmonary oedema using dual-frequency electrical impedance", *Medical & Biological Engineering & Computing*, 36(4), (Jul. 1998), 461-468.
Raggueneau, J. L., et al., "Monitoring of intracellular and extracellular hydric compartments by body impedance", *Anesth Anal. Rean*, vol. 36, (1979), 439-443.
Ramos, M. U, et al., "Transthoracic electric impedance. A clinical guide of pulmonary fluid accumulation in congestive heart failure", *Minnesota Medicine*, 58(9), (Sep. 1975), 671-676.
Rosborough, J. P., et al., "Electrical Therapy for Pulseless Electrical Activity", *NASPE*, 23(4), Part II, (Abstract), (Apr. 2000), p. 591.
Saunders, C. E., "The Use of Transthoracic Electrical Bioimpedance in Assessing Thoracic Fluid Status in Emergency Department Patients", *American Journal of Emergency Medicine*, 6(4), (Jul. 1988), 337-340.
Schuster, C. J, et al., "Application of Impedance Cardiography in Critical Care Medicine", *Resuscitation*, vol. 11, (1984), 255-274.
Schwartzman, D., et al., "Serial Defibrillation Lead Impedance in Patients with Epicardial and Nonthoracotomy Lead Systems", *Journal of Cardiovascular Electrophysiology*, 7(8), (Aug. 1996), 697-703.
Segev, G., et al., "B-Type Natriuretic Peptide: a Novel Clinical Tool for Diagnosis and Management of Heart Failure", *Hospital Physician*, (Sep. 2003), 19-24.
Shochat, M., et al., "Internal thoracic impedance monitoring: a new prospect in acute heart failure", European Heart Journal, 25(Supp), (Aug.-Sep. 2004), p. 72.
Shoemaker, William C, et al., "Multicenter trial of a new thoracic electrical bioimpedance device for cardiac output estimation", Critical Care Medicine, 22(12), (Dec. 1994), 1907-1912.
Smith, R. M., et al., "Canine thoracic electrical impedance with changes in pulmonary gas and blood volumes.", Journal of Applied Physiology, 53(6), (Dec. 1982), 1608-13.

Spinale, F. G., et al., "Noninvasive estimation of extravascular lung water using bioimpedance.", The Journal of Surgical Research, 47(6), (Dec. 1989), 535-40.
Sra, J S, et al., "Cardiac pacing during neurocardiogenic (vasovagal) syncope", J Cardiovasc Electrophysiol., 6(9), (Sep. 1995), 751-60.
Stadler, R., et al., "Automated detection of decreases in intrathoracic impedance to predict CHF hospitalization", Abstract 263, 26(4 pt II), Abstract 16, (Apr. 2003), 932.
Staub, N. C., "The measurement of lung water content.", The Journal of Microwave Power, 18(3), (Sep. 1983), 259-63.
Tang, W., "Assessment of total body water using bioelectrical impedance analysis in neonates receiving intensive care", Arch Dis Child Fetal Neonatal Ed., 77(2), (Sep. 1997), F123-F126.
Tempel, G., et al., "Transthoracic electrical impedance in anaesthesia and intensive care.", Resuscitation, 6(2), (1978), 97-105.
Thakur, R. K., et al., "Pericardial Effusion Increases Defibrillation Energy Requirement", *Pacing Clin Electrophysiol.*, 16(6), (Jun. 1993), 1227-1230.
Vainshtein, G. B, et al., "The Functioning of the Cerebral Circulation System in Hyperthermia in Rabbits", *Fiziol Zh SSSR Im I M Sechenova*, 75(11), (Nov. 1989), 1608-1614.
Van De Water, J. M., et al., "Monitoring the Chest with Impedance", *Chest*, 64(5), (Nov. 1973), 597-603.
Viirola, H., et al., "Controlled growth of antimony-doped tin dioxide thin films by atomic layer epitaxy", *Thin Solid Films*, 251, (Nov. 1994), 127-135.
Viirola, H., et al., "Controlled growth of tin dioxide thin films by atomic layer epitaxy", *Thin Solid Films*, 249(2), (Sep. 1994), 144-149.
Visokay, M. R., "Application of HfSiON as a gate dielectric material", *Applied Physics Letters*, 80(17), (Apr. 2002), 3183-3185.
Wang, L., et al., "Impedance based prediction of CHF admission precedes symptoms in heart failure patients", *Heartrhythm : the Official Journal of the Heart Rhythm Society*, 1(Suppl 1), Abstract 679, (2004), p. S213.
Wang, L., et al., "Prediction of CHF hospitalization by ambulatory intrathoracic impedance measurement in CHF patients is feasible using pacemaker or ICD lead systems", *Pacing and Clinical Electrophysiology*, 26(4 pt. II), (Abstract 123), (Apr. 2003), p. 959.
Wang, Li, et al., "Multiple Sources of the Impedance Cardiogram Based on 3-D Finite Difference Human Thorax Models", *IEEE Transactions on Biomedical Engineering*, 42(2), (Feb. 1995), 141-148.
Wuerz, R. C., et al., "Effects of prehospital medications on mortality and length of stay in congestive heart failure", *Annals of Emergency Medicine*, 21(6), (Jun. 1992), 669-74.
Yu, C., et al., "Changes in device based thoracic impedance in decompensating congestive heart failure", *Circulation*, 104(17 supplement), (Abstract 1994), (2001), II-419.
Yu, C. M., et al., "Correlation of device-based intra-thoracic impedance and patient fluid status during intravenous diuretic therapy in acute CHF", *European Heart Journal*, 23(*Abstract Supplement*), (2002), p. 158.
Yu, C., et al., "Device-based intra-thoracic impedance correlates with fluid status and provides automated prediction of CHF hospitalization", *Journal of Cardiac Failure*, 10(4 Suppl), (Abstract 354), (2004), p. S113.
Yu, C., et al., "Early warning of CHF hospitalization by intra-thoracic impedance measurement in CHF patients with pacemakers", *Pacing and Clinical Electrophysiology: PACE*, 24(4 pt II), Abstract 19, (2002), p. 527.
Yu, C. M., et al., "Impedance measurements from implanted devices provide automated prediction of CHF hospitalization", *European Heart Journal*, 25(*Supp*), (Aug.-Sep. 2004), p. 27.
Yu, C. M., et al., "Intrathoracic impedance: A surrogate measure of fluid retention and predictor of hospitalization in patients with heart failure", Journal of the American College of *Cardiology*, 41(*6 Supplement A*), (Abstract 1206-70), (2003), p. 210A.
Yu, Cheuk-Man, et al., "Early warning of CHF hospitalization by intra-thoracic impedance measurement in CHF patients with pacemakers", *Pacing and Clinical Electrophysiology*, 24, (Apr. 2001), p. 19.

Zellner, J. L., et al., "Bioimpedance: a novel method for the determination of extravascular lung water.", *The Journal of Surgical Research*, 48(5), (May 1990), 454-459.

Zima, E., "Intracardiac impedance in biventricular electrode configuration for left ventricular volume monitoring", *European Heart Journal*, 25(*Supp*), (Aug.-Sep. 2004), p. 165.

CALIBRATION OF IMPEDANCE MONITORING OF RESPIRATORY VOLUMES USING THORACIC D.C. IMPEDANCE

CLAIM OF PRIORITY

This application is a division of U.S. patent application Ser. No. 11/114,661, filed Apr. 26, 2005, now issued as U.S. Pat. No. 7,603,170, which is incorporated herein by reference in its entirety.

CROSS-REFERENCE TO RELATED APPLICATION

This application is related to, commonly assigned U.S. patent application Ser. No. 10/921,503, entitled "THORACIC IMPEDANCE DETECTION WITH BLOOD RESISTIVITY COMPENSATION," filed on Aug. 19, 2004, now issued as U.S. Pat. No. 7,387,610, and is incorporated herein by reference.

TECHNICAL FIELD

The field generally relates to implantable medical devices and, in particular, but not by way of limitation, to systems and methods for monitoring respiratory volumes using electrical measurements of trans-thoracic impedance.

BACKGROUND

Implantable medical devices (IMDs) are devices designed to be implanted into a patient. Some examples of these devices include cardiac rhythm management (CRM) devices such as implantable pacemakers, implantable cardioverter defibrillators (ICDs), and devices that include a combination of pacing and defibrillation. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Congestive heart failure (CHF) is a disease that reduces the ability of the ventricles of the heart to contract or relax. This results in an inadequate amount of blood being pumped into circulation. The reduced ability to move blood from veins to arteries may increase volume and pressure within the heart leading to heart failure progression. If left unchecked, CHF can lead to death. Respiratory function of a patient changes as the disease progresses. Monitoring aspects of respiration, such as the lung tidal volume, gives an indication of the progression of the disease.

SUMMARY

The present inventors have recognized a need for improved monitoring of lung tidal volumes, or breathing volumes, using medical devices. This document discusses, among other things, systems and methods for monitoring lung tidal volume. A system embodiment comprises an implantable medical device that includes a trans-thoracic impedance measurement circuit. The trans-thoracic impedance measurement circuit provides a trans-thoracic impedance signal of a subject. A controller is coupled to the trans-thoracic impedance circuit. The controller extracts a respiration signal from the trans-thoracic impedance signal, measures a breathing volume of the subject using the amplitude of the respiration signal and a breathing volume calibration factor, computes an adjusted breathing volume calibration factor, and computes a calibrated breathing volume using the adjusted breathing volume calibration factor. The adjusted breathing volume calibration factor is computed using a reference baseline value of the trans-thoracic impedance and a measured change from the reference baseline value of the trans-thoracic impedance.

A method embodiment comprises measuring breathing volume of a patient using an implantable medical device, detecting a change in DC trans-thoracic impedance, and adjusting a breathing volume calibration factor used by the implantable medical device in measuring the breathing volume in accordance with the change in DC trans-thoracic impedance.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The present application discusses, among other things, systems and methods for monitoring lung tidal volume, or breathing volume. Illustrative examples of methods of monitoring lung tidal volume by measuring trans-thoracic impedance are described in Hartley et al. U.S. Pat. No. 6,076,015 entitled "RATE ADAPTIVE CARDIAC RHYTHM MANAGEMENT DEVICE USING TRANSTHORACIC IMPEDANCE," which is incorporated herein by reference.

As discussed above, congestive heart failure (CHF) involves the reduced ability to move blood from veins to arteries. Insufficient flow from veins to arteries allows blood to build up in the pulmonary veins. This leads to pulmonary edema, that is, fluid accumulation in the lungs. As the fluid accumulates, the increased fluid may cause the impedance of current pathways through the lungs to be reduced. This in turn causes the amplitude of an impedance signal to be reduced for a given respiration level. The present inventors have recognized that the effect of pulmonary edema needs to be considered when calculating tidal volume-based performance measures of a patient's pulmonary function.

Figure 1:
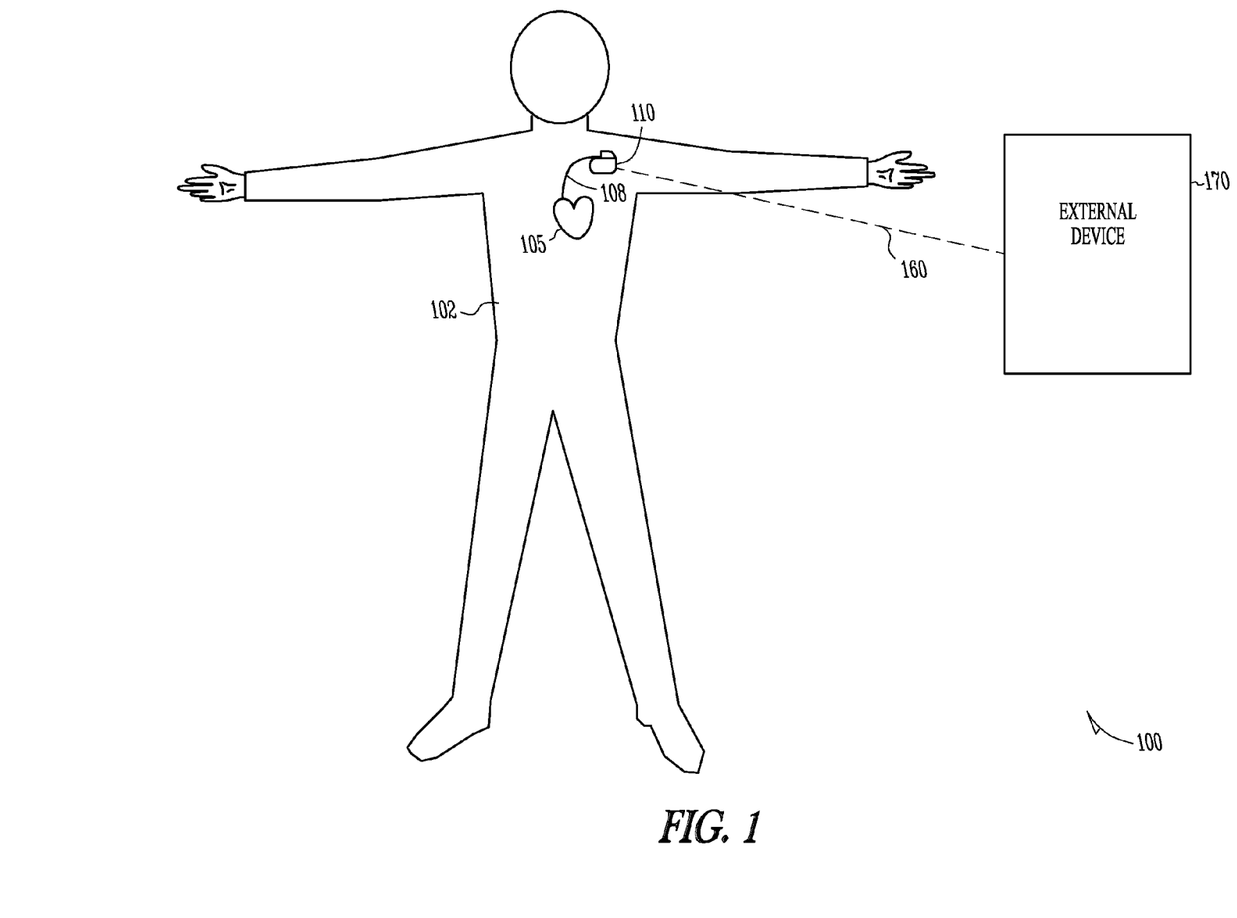
FIG. 1 illustrates an embodiment of portions of a system that uses an implantable medical device.

FIG. 1 illustrates an embodiment of portions of a system 100 that uses an implantable medical device (IMD) 110. As one example, the system 100 shown is used to treat a cardiac arrhythmia. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion defibrillation, pacing, resynchronization therapy, or combinations thereof to at least one chamber of the heart 105. The IMD 110 typically includes components that are enclosed in a hermetically-sealed canister or "can." Additional electrodes may be located on the can, or on an insulating header extending from the can, or on other portions of IMD 110, such as for providing unipolar pacing energy, defibrillation energy, or both in conjunction with the electrodes disposed on or around heart 105. The lead 108 or leads and electrodes are also typically used for sensing electrical activity of a heart 105.

Figure 2A:
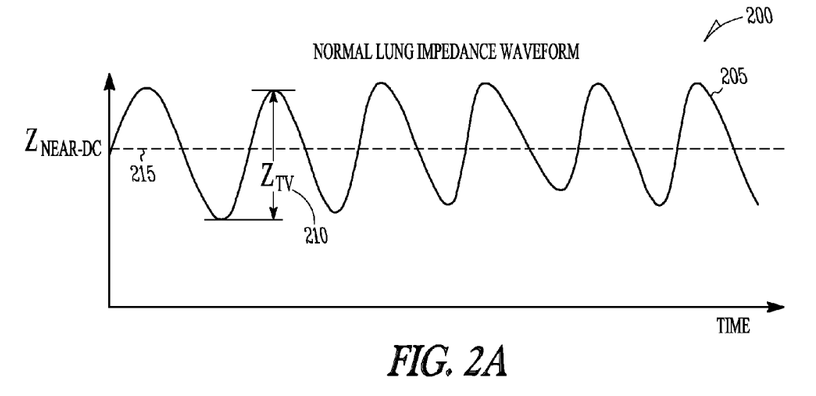
FIGS. 2A and 2B show graphical representations of trans-thoracic impedance waveforms.

Hartley et al., describes obtaining a trans-thoracic impedance signal of a patient using an IMD. A test current is applied between electrodes placed across a thorax region of a patient. This test current typically uses a sufficiently small magnitude, or a sufficiently high frequency, or both, to avoid interference with cardiac activity. Measuring the resulting voltage between the electrodes provides a trans-thoracic impedance signal for the patient. Signal processing circuitry extracts lung tidal ventilation information by filtering the impedance signal. FIG. 2A shows a graphical representation 200 of a trans-thoracic impedance vs. time waveform 205 of the lung tidal ventilation information for a normal lung. The peaks and valleys in the impedance signal correspond to breathing cycles of the patient.

$Z_{DC}$ 215 is the DC artifact of the trans-thoracic impedance signal with variations at frequencies lower than the respiration component of the trans-thoracic impedance signal. In this document, the term "DC" component of the trans-thoracic impedance signal refers not just to zero frequency, but also includes signal frequencies below a cutoff frequency having a value of about 0.1 Hz, such as at signal frequencies between 0 Hz and 0.05 Hz, because the cardiac stroke and respiration components of the trans-thoracic impedance signal lie at higher frequencies. The rate at which the impedance waveform 205 crosses the DC level 215 in either the positive or negative direction corresponds to the rate of breathing cycles of the patient measured in breaths per unit of time, such as breaths/minute for example. This is often referred to as the ventilation rate (VR), respiration rate, or breathing rate.

$Z_{TV}$ 210 is an amplitude of the respiration modulation component of the trans-thoracic impedance signal. It indicates the cyclic change in impedance resulting from a patient's breathing. The signal represents the impedance variation of the patient measured in ohms/breath. A calibration factor (CF) is used to translate the impedance information from ohms/breath to a measure of volume per breath. For example, if the calibration factor is a measure of liters-of-air per ohm, then multiplying the impedance measure of ohms/breath by the calibration factor of liters/ohm results in a measure of liters/breath. The measure of lung volume per breath is often referred to as lung tidal volume (TV). Thus, $$\text{TV(volume/breath)} = Z_{TV}(\text{ohms/breath}) * \text{CF(volume/ohms)}. \quad \text{Equ. 1.}$$

Lung tidal volume is one measure of metabolic need of a patient. For example, increased lung volumes may indicate that a patient requires an increased pacing rate because of an increased level of physical activity. A calibration factor for the impedance measurements can be set after implant of the IMD. For example, a clinician can run tests to measure the volume of a deep breath of a patient. This volume is then divided by the maximum peak-to-valley value of impedance to determine a calibration factor, which is then programmed into the IMD. Hartley et al. further describes how lung tidal volume is useful in determining minute ventilation (MV), where MV is function of tidal volume (TV) and ventilation rate (VR). MV measures a patient's air flow rate (e.g. liters/minute), and has been shown to correlate well with a patient's metabolic need for a change in heart rate. Hartley et al. describes the usefulness of MV in cardiac rhythm management devices (CRMs) such as rate adaptive pacemakers.

Figure 2B:
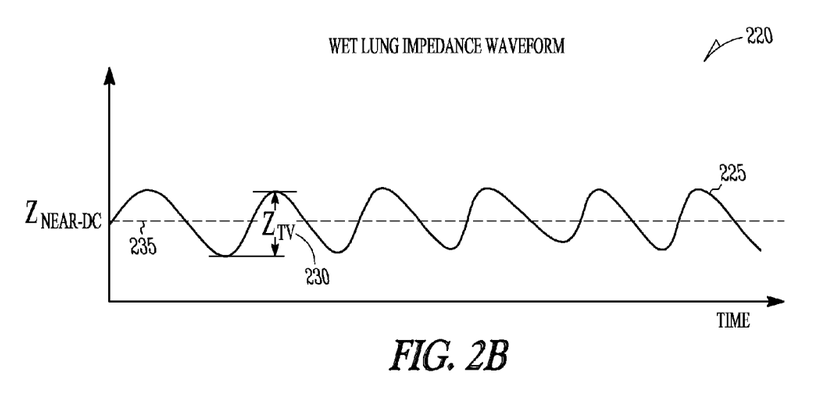

However, the sensitivity of impedance measurements to respiratory volumes may change with pulmonary edema. As fluid in trans-thoracic tissue builds up as heart disease progresses, the impedance of current pathways through the lungs may be reduced. This reduces the respiration amplitude of an impedance signal for a given respiration level. The impedance may be reduced because the fluid that builds up contains electrolytes that act to "short circuit" the current pathways. This phenomenon is shown by a comparison of FIG. 2A with FIG. 2B. FIG. 2B shows a graphical representation 220 of a trans-thoracic impedance waveform 225 corresponding to a "wet" lung with fluid build-up. Even though the patient may be breathing just as deeply as in FIG. 2A, the lower amplitude makes it appear that the patient is not breathing as deeply. The graph 220 illustrates that both $Z_{TV}$ 230 and $Z_{DC}$ 235 are reduced from the graph 200 in FIG. 2A. This reduction in amplitude of the impedance signal could be mistaken for a change in depth of respiration even though it in fact results from a change in impedance due to fluid accumulation. Therefore, it could result in misdiagnosis of a patient.

This problem is alleviated or avoided by adjusting the calibration factor. In one example, an adjusted calibration factor is determined using a reference baseline value of trans-thoracic impedance and a measured change from the reference baseline value. In some embodiments, the calibration factor is adjusted as a function that includes a reference DC impedance value and a measured DC impedance value. The reference DC impedance, $Z_{DC,ref}$, is a baseline DC impedance such as $Z_{DC}$ in FIG. 2A. The measured DC impedance refers to a change in $Z_{DC}$ from the baseline, such as the change resulting in the value of $Z_{DC}$ in FIG. 2B. A tidal volume (TV) measurement is then re-calibrated using the adjusted calibration factor. If $TV_{RAW}$ is an unadjusted (or raw) value of TV calculated as in Equation 1 above, then a re-calibrated tidal volume $TV_{CAL}$ can be determined as a function that includes the raw TV, the reference DC impedance, and the measured DC impedance, or $$TV_{CAL} = f\{TV_{RAW}, Z_{DC}, Z_{DC,ref}\} \quad \text{Equ. 2}$$

In some of the embodiments, the calibration factor is adjusted by the ratio of the reference DC impedance to the measured DC impedance, or $Z_{DC,ref}/Z_{DC}$, i.e., $$TV_{CAL} = Z * CF * (Z_{DC,ref}/Z_{DC}) \quad \text{Equ. 3}$$

The tidal volume measurement is thus re-calibrated to take into account a new level of fluid build-up. Thus, if the impedance is reduced due to buildup of fluid in the trans-thoracic tissue, $Z_{DC}$ is less than $Z_{DC,ref}$ and the calibration factor is increased to correct for the reduction.

If the measurement is not automatically recalibrated as fluid builds-up, recalibration will not occur or at best will be postponed until a patient's next visit to a clinician. This could result in a long period of time where the impedance measurements do not accurately reflect a patient's true respiration. In one example, if the medical device uses a measure of trans-thoracic impedance in deciding whether to automatically adjust a pacing rate, an increased metabolic need of the patient may result in an inadequate increase in the pacing rate. Thus, the medical device would not be performing optimally. Similarly, patient diagnostic measures relying on impedance-derived estimates of tidal volume may inaccurately report shallow breathing, even though the breathing is normal.

According to some embodiments, the problem of the reduction in amplitude of the impedance signal is alleviated or avoided by adjusting the test current applied between the electrodes placed across a thorax region of a patient. If fluid builds up in the trans-thoracic tissue, the measured voltage, V, due to a given current will be reduced resulting in a reduced measured DC impedance value $Z_{DC}$. This reduction can be corrected by increasing the test current until the DC voltage, $V_{DC}$, equals $V_{DC,ref}$ or by increasing the current by the ratio of $Z_{DC,ref}/Z_{DC}$. The adjusted impedance measurements are used to calculate tidal volume, TV, in Equation 1. Conversely, if the DC impedance value increases, the test current is decreased until $V_{DC}$ equals $V_{DC,ref}$ or by decreasing the current by the ratio of $Z_{DC,ref}/Z_{DC}$. While these embodiments are more complex to implement than recalibrating CF, the embodiments could lower the average energy used by the impedance sensor if lower test current is used, and they also have the advantage of raising the measurable voltage if the current is being shunted by fluid buildup.

Figure 3:
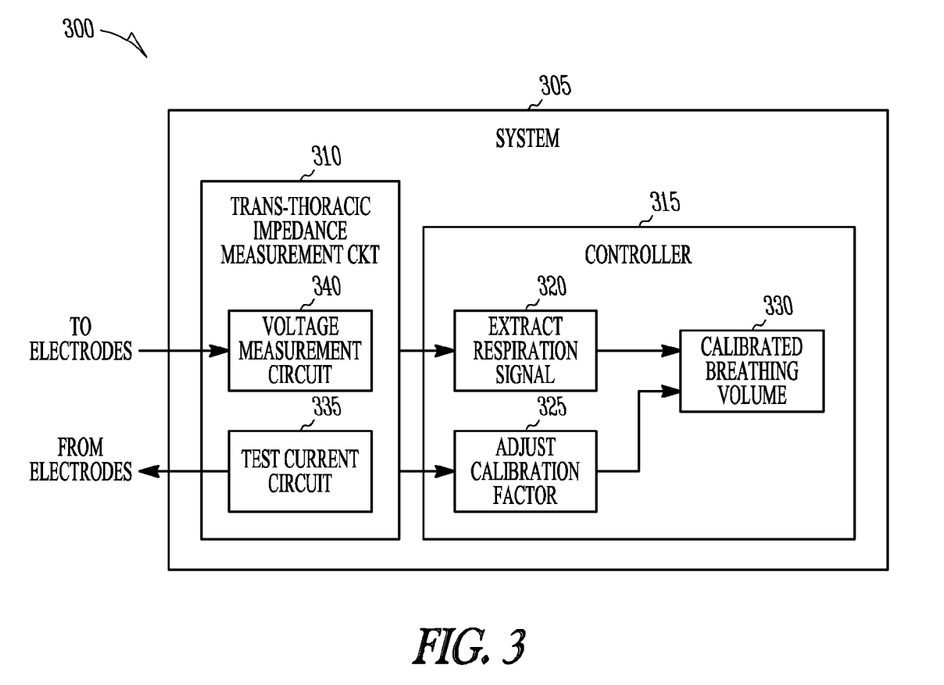
FIG. 3 is a block diagram of portions of an embodiment of a system for monitoring lung tidal volume.

FIG. 3 is a block diagram of portions of a system 300 for monitoring lung tidal volume. In this example, the system 300 comprises an implantable medical device (IMD) 305 that includes a trans-thoracic impedance measurement circuit 310 and a controller 315 coupled to the trans-thoracic impedance circuit 310. The trans-thoracic impedance measurement circuit 310 provides a trans-thoracic impedance signal of a subject. The trans-thoracic impedance signal typically contains other physiological artifacts in addition to respiration, such as artifacts from heart contractions. The controller 315 extracts a respiration signal 320 from the trans-thoracic impedance signal, such as by frequency filtering of the trans-thoracic impedance signal. In an embodiment, extracting the respiration signal 320 includes attenuating frequencies of the impedance signal that are higher than 0.5 Hz. In some embodiments, the frequency cutoff is a variable that is based, at least in part, on a patient's heart rate. In some embodiments, the respiration signal 320 is filtered using dedicated hardware filtering circuits, and in some embodiments the respiration signal 320 is filtered using digital signal processing by the controller 315 or elsewhere. The controller 315 is typically operable by executing or interpreting instructions in software, firmware, hardware, or any combination of software, firmware, or hardware.

The controller 315 also measures a breathing volume of the subject using the amplitude of the respiration signal 320 and a breathing volume calibration factor as discussed previously. The breathing volume calibration factor is computed using a reference baseline value of the DC trans-thoracic impedance. If the controller 315 measures a change from the reference baseline value of the DC trans-thoracic impedance, the controller 315 computes an adjusted breathing volume calibration factor 325 using the measured change. The controller 315 then computes a calibrated breathing volume 330 using the adjusted breathing volume calibration factor 325. In some of the embodiments, the adjusted breathing volume calibration factor includes a ratio of a reference DC trans-thoracic impedance to a measured change in DC trans-thoracic impedance.

According to some embodiments, the IMD 305 of the system 300 further includes a storage circuit coupled to the controller 315 to store the reference baseline impedance value of the DC trans-thoracic impedance. The controller 315 adjusts a breathing volume calibration factor in response to a measured change in impedance value from the reference baseline impedance value. In some further embodiments, in which measurements of the trans-thoracic impedance include a reference DC trans-thoracic impedance, the IMD 305 includes storage for storing trends in measured DC trans-thoracic impedance values. In some embodiments, trends in breathing volumes are stored.

According to some embodiments, the IMD 305 includes a posture detecting circuit coupled to the controller 315. One example of a posture detecting circuit is an accelerometer. An amount of fluid buildup in a patient's lungs may change with a patient's posture. For example, a patient who is lying down may have more fluid buildup than when the patient is upright.

In some embodiments, the controller adjusts the breathing volume calibration without regard to changes in posture of a patient. In some embodiments, the controller 315 detects when a patient is in one posture and only adjusts a breathing volume calibration factor based on measurements while the patient is in that posture. This is to avoid recalibrating the breathing volume calibration factor when the patient changes posture. Limiting the recalibration to only one posture removes this variation due to posture. For example, assume the controller 315 is programmed to only detect changes from the reference baseline value of a DC component of a trans-thoracic impedance while the patient is in an upright position. If the controller 315 detects a change from the reference baseline value, the controller then determines if the patient is upright and can use the computed change. If the patient is upright, the controller 315 uses the computed change to adjust the breathing volume calibration factor. If the patient is lying down, the controller 315 does not adjust the breathing volume calibration factor. In another example, the controller 315 is enabled to detect changes from the reference baseline value only while the patient is in one posture.

In some embodiments, the controller 315 tracks changes in DC trans-thoracic impedance for a plurality of postures. As an example, consider the relatively simple case of tracking changes for two postures. In the example, the controller 315 stores a first reference baseline impedance value associated with a first posture, such as an upright posture, and a second reference baseline impedance value associated with a second posture, such as lying down. The controller 315 adjusts an upright calibration factor 325 when a measured change from the first reference baseline value is detected while a patient is upright. The controller 315 also adjusts a lying down calibration factor 325 when a measured change from the second reference baseline value is detected while the patient is lying down. In this way, the controller 315 provides a calibrated measurement of tidal volume while the patient is upright or lying down. In some embodiments the controller 315 uses hysteresis before adjusting the calibration factor 325. This is useful to account for changes in a patient's posture that are only temporary.

Some embodiments of the trans-thoracic impedance measurement circuit 310 include a test current circuit 335 coupled to the controller 315, and a voltage measurement circuit 340 coupled to the controller 315. A plurality of implantable electrodes is coupled to the test current circuit 335 and the voltage measurement circuit 340. The test current circuit 335 delivers a test current using the implantable electrodes, and the voltage measurement circuit 340 measures a voltage resulting from the test current. The resulting voltage may be measured using electrodes that are the same or different from the electrodes used to deliver the test current.

Figure 4:
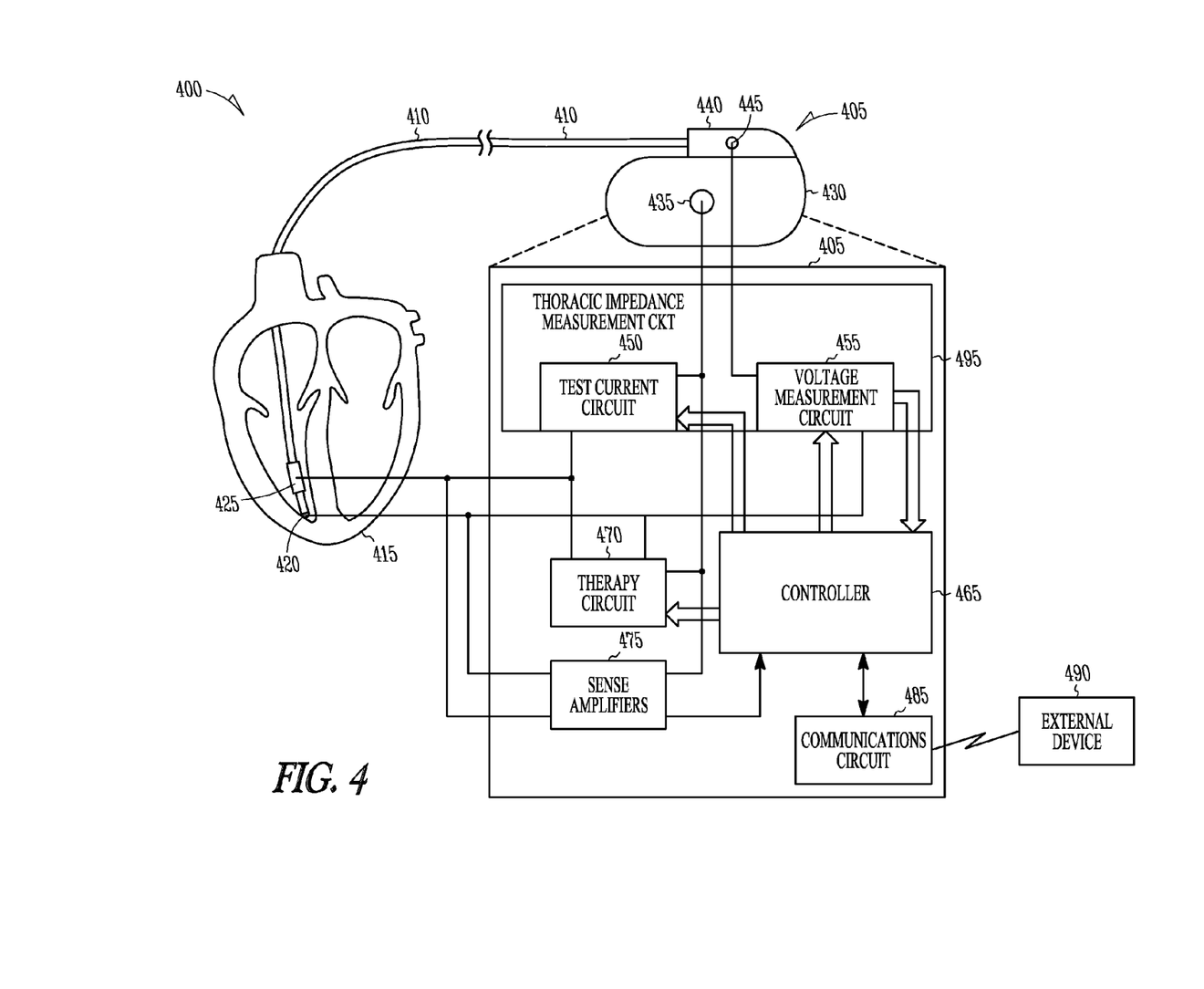
FIG. 4 is an illustration of portions of an embodiment of a system for monitoring lung tidal volume that includes a cardiac rhythm management device.

FIG. 4 is an illustration of portions of a system 400 for monitoring lung tidal volume. In this example, the system 400 includes an IMD 405 that is a cardiac rhythm management device. The IMD 405 is coupled to heart 415 by a cardiac lead 410 that includes lead tip and ring electrodes 420, 425. The IMD 405 includes components that are enclosed in a hermetically-sealed canister or "can" 430. Additional electrodes include an electrode 435 located on the can 430 and a header electrode 445 located on the insulating header 440. A therapy circuit 470 is used to provide pacing and/or defibrillation energy in conjunction with the electrodes 420, 425 disposed on or around heart 415. The lead 410 and lead electrodes 420, 425 are used in conjunction with sense amplifiers 475 for sensing electrical activity of a heart 415.

The IMD 405 includes a trans-thoracic impedance measurement circuit 495 coupled to a controller 465. The impedance measurement circuit 495 includes a test current circuit 450 and a voltage measurement circuit 455. In the embodiment shown, the test current is delivered using the ring electrode 425 and the can electrode 435. The voltage is measured using tip electrode 420 and the header electrode 445. Embodiments can use any combination of electrodes to deliver the current and measure the voltage. For example, the electrodes used in FIG. 4 to deliver the test current and those to measure the test voltage could be swapped. Or, some or all of the electrodes used to deliver the current could be the same as the electrodes to measure the voltage. For example, the test current could be delivered from the ring electrode 425 to the can electrode 435 and the voltage could be measured from the tip electrode 420 to the can electrode 435, or the test current could be delivered between the tip electrode 420 and the header electrode 445, and the voltage could measured using the same two electrodes 420, 445.

According to some embodiments, the system 400 further includes an external device 490 operable to communicate with the IMD 405 using the communication circuit 485. The communication is through wireless signals such as telemetry signals or RF signals. In an embodiment, the IMD 405 communicates information related to breathing volume to the external device 490. This information may include a calibrated breathing volume, or it may only include the impedance information that is related to breathing and the external device 490 computes the calibrated breathing volume. In one example, the external device 490 includes a display, and the external device 490 displays breathing volume information obtained from the trans-thoracic impedance signal. In some embodiments, displayed breathing volume information includes a histogram of DC trans-thoracic impedance of the patient. In another embodiment, the displayed breathing volume information includes trending information of DC trans-thoracic impedance. In another embodiment, the displayed breathing volume information includes an indication of fluid accumulation in a patient's lungs. According to some embodiments, the external device 490 is part of, or in communication with, a computer network such as a hospital computer network or the internet.

Figure 5:
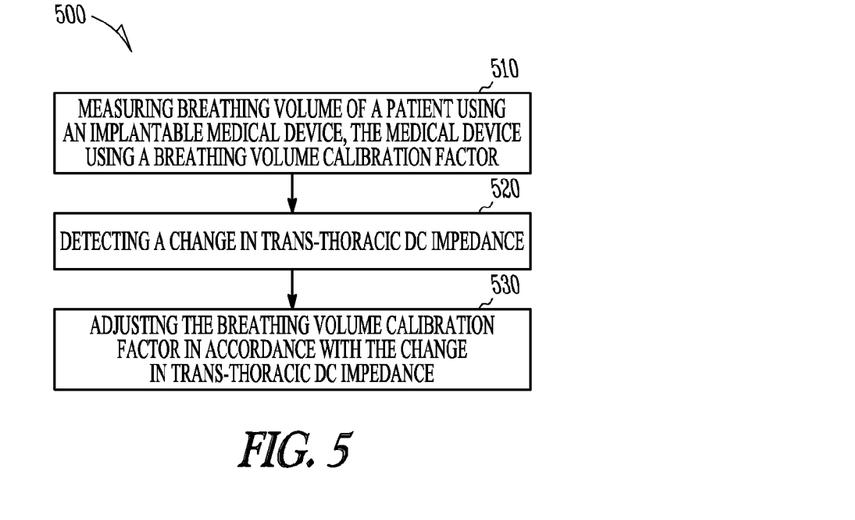
FIG. 5 is a block diagram of an embodiment of a method for monitoring lung tidal volume.

FIG. 5 is a block diagram of an embodiment of a method 500 for monitoring lung tidal volume. At 510, a breathing volume of a patient is measured using an IMD. The IMD uses a breathing volume calibration factor in measuring the breathing volume. In an embodiment, the IMD is a cardiac rhythm management device (CRM). In one example, a therapy delivered by the CRM device, such as a pacing rate, can be changed in accordance with the measured breathing volume.

In another embodiment, the breathing volume is measured using trans-thoracic impedance. In some embodiments, measuring trans-thoracic impedance includes delivering a test current using first and second implantable electrodes, and measuring a voltage resulting from the test current using third and fourth implantable electrodes. In some of the embodiments, at least one of the first and second implantable electrodes is the same as one of the third and fourth implantable electrodes. Thus, embodiments include measuring the impedance using four, three, or two electrodes. In some embodiments, using a breathing volume calibration factor includes using the breathing volume calibration factor to associate a measurement of ohms-per-breath with respiratory volume-per-breath. For example, extraction of a respiration signal waveform as in FIGS. 2A, 2B above results in a measurement of ohms/breath. Multiplying ohms/breath by a calibration factor with units of liters/ohm results in a measurement of liters/breath.

At 520, a change is detected in DC trans-thoracic impedance. At 530, the breathing volume calibration factor is adjusted in accordance with the change in DC trans-thoracic impedance. In some embodiments, the breathing volume calibration factor is adjusted using a function of a reference DC impedance and a measured DC impedance, and measuring breathing volume includes calibrating a raw measurement of breathing volume using the adjusted breathing volume calibration factor. In one embodiment, the function of a reference DC impedance and a measured DC impedance includes a ratio of the reference DC impedance to the measured DC impedance ($Z_{DC,ref}/Z_{DC}$).

According to some embodiments, detecting a change in DC trans-thoracic impedance includes monitoring DC trans-thoracic impedance over time. This includes monitoring impedance with a sampling period of seconds, minutes, hours, or days. It also includes monitoring impedance for an interval of time or monitoring constantly. In some of the embodiments, impedance is measured under the same conditions with respect to posture to reduce the effect of changes in posture on the measurement. In an example, time of day is used to measure impedance according to a circadian cycle when a patient is most likely to be lying down.

In some embodiments, detecting a change in DC trans-thoracic impedance includes determining a baseline DC trans-thoracic impedance and detecting changes in impedance from the baseline DC trans-thoracic impedance. In some embodiments, the measurements are made under the same posture conditions and detecting a change in DC trans-thoracic impedance includes determining a first baseline DC trans-thoracic impedance for a first patient posture, such as an upright posture, and a second DC trans-thoracic impedance for a second patient posture, such as lying down. Changes in impedance from the first baseline impedance are monitored when the patient is in the first posture. Changes in impedance from the second baseline impedance are monitored when the patient is in the second posture. Posture can be determined from a posture sensor, such as a two-axis accelerometer, or posture can be deduced, such as from time of day according to a circadian cycle. A clock circuit is used to determine time of day.

According to some embodiments, the method further includes storing trending information related to DC trans-thoracic impedance. In some of the embodiments, the method further includes communicating the trending information to an external device for display. In another embodiment, the method includes communicating DC trans-thoracic impedance information to an external device connected to a computer network such as a hospital computer network or the internet.

Figure 6:
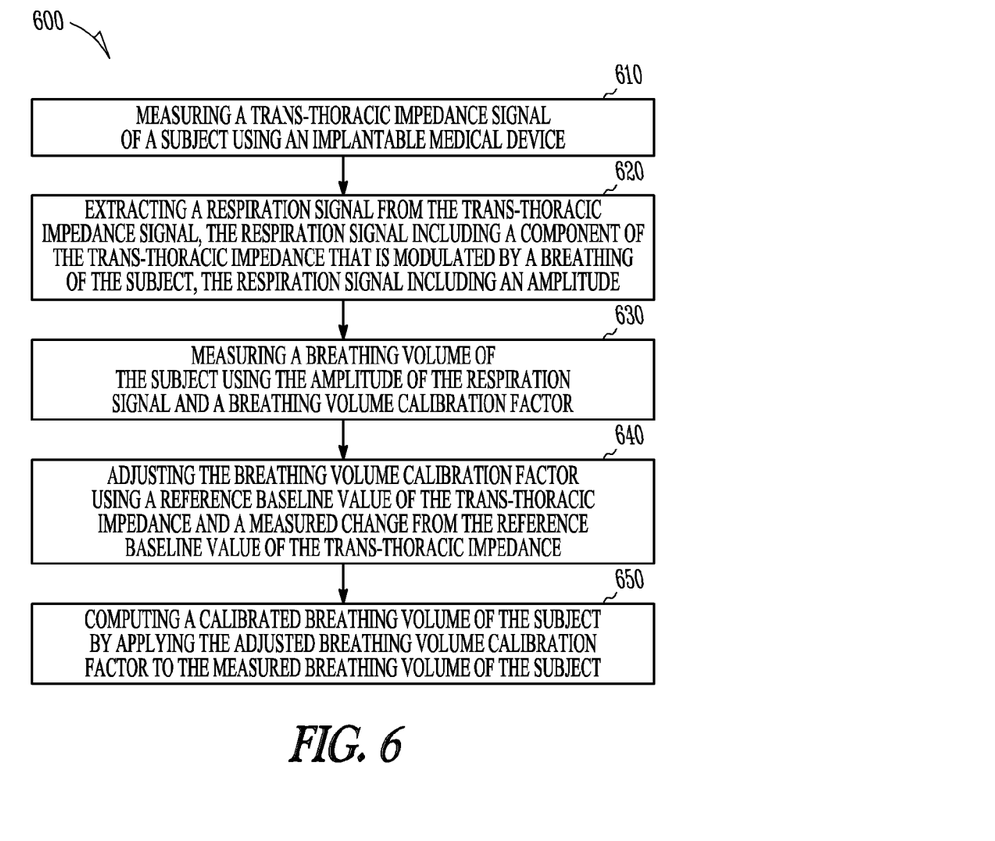
FIG. 6 is a block diagram of another embodiment of a method for monitoring lung tidal volume.

FIG. 6 is a block diagram of another embodiment of a method 600 for monitoring lung tidal volume. At 610, a trans-thoracic impedance signal of a subject is measured using an implantable medical device (IMD), such as by using any of the systems or methods described previously. At 620, a respiration signal is extracted from the trans-thoracic impedance signal. The respiration signal includes a component of the trans-thoracic impedance that is modulated by a breathing of the subject. The trans-thoracic impedance signal includes components from other sources such as heart contractions. Signal processing methods are used to extract the respiration signal. In some embodiments, the respiration signal is extracted by filtering the impedance signal. In an embodiment, the respiration signal is extracted by attenuating frequencies higher than 0.5 Hz in the impedance signal. In some embodiments, the frequency cutoff is a heart rate dependent variable.

At 630, a breathing volume of the subject is measured using the amplitude of the respiration signal and a breathing volume calibration factor. Some embodiments include measuring a breathing volume of the subject using the peak-to-peak amplitude of the respiration signal. The breathing volume calibration factor is used to convert an impedance-per-breath measurement of the respiration signal into a volume-per-breath measurement. In some embodiments, the breathing volume is measured by combining the measurement from the respiration signal with other measurements. Some of the embodiments include using a measure of hematocrit in blood of the subject. Some of the embodiments include using a measure of resistivity of blood within a heart. Systems, methods, and devices that detect changes in blood resistivity are described in co-pending, commonly assigned U.S. patent application Ser. No. 10/921,503, entitled "THORACIC IMPEDANCE DETECTION WITH BLOOD RESISTIVITY COMPENSATION," filed on Aug. 19, 2004 which is incorporated herein by reference.

At 640, the breathing volume calibration factor is adjusted using a reference baseline value of the DC trans-thoracic impedance and a measured change from this reference baseline value. At 650, a calibrated breathing volume of the subject is computed by applying the adjusted breathing volume calibration factor to the measured breathing volume of the subject. In some embodiments, the calibration factor is adjusted according to a ratio of a reference baseline DC trans-thoracic impedance to a measured DC trans-thoracic impedance, and wherein the breathing volume is calibrated by multiplying the measured breathing volume by the adjusted calibration factor. In some embodiments, the breathing volume calibration factor is adjusted by combining the measurement from the respiration signal with other measurements. Some of the embodiments include adjusting the calibration factor using a measure of a change in hematocrit in blood of the subject. Some of the embodiments include adjusting the calibration factor using a measure of a change in resistivity of blood within a heart. Some of the embodiments include adjusting the calibration factor using a measure of a change in posture of a patient. In some of the embodiments, the breathing volume calibration factor is adjusted by combining the measurement from the respiration signal with any combination that includes a measured change in hematocrit, blood resistivity, or patient posture. By adjusting a calibration for respiratory sensing, a patient's respiration can be monitored more accurately over varying degrees of pulmonary edema. Accurate monitoring of respiration of a patient experiencing pulmonary edema leads to improved patient management and improved patient care. Although trans-thoracic impedance has been described as a measurement between an implanted device and a cardiac lead, other methods of trans-thoracic impedance measurement may be utilized without departing from the scope of this invention. For example, measurements between any two or more electrodes may be used. Further, measurements within any portion of the thoracic cavity are within the scope of this invention.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:
1. A method comprising:
   detecting a change in direct current (DC) trans-thoracic impedance;
   adjusting a breathing volume calibration factor in accordance with the change in DC trans-thoracic impedance, wherein the breathing volume calibration factor translates a measure of impedance to a measure of breathing volume, and the adjusted breathing volume calibration factor includes a ratio of a reference DC trans-thoracic impedance to a more recently measured value of the DC trans-thoracic impedance; and measuring breathing volume of a patient using the implantable medical device, the medical device adjusting the measured breathing volume using the breathing volume calibration factor.

2. The method of claim 1, wherein adjusting the breathing volume calibration factor includes adjusting using the ratio of a reference DC impedance and the more recently measured DC impedance, and wherein measuring breathing volume includes calibrating a raw measurement of breathing volume using the breathing volume calibration factor.

3. The method of claim 1, wherein measuring breathing volume includes measuring trans-thoracic impedance.

4. The method of claim 1, wherein detecting the change in DC trans-thoracic impedance includes monitoring DC trans-thoracic impedance over time.

5. The method of claim 1, wherein the breathing volume calibration factor associates a measurement of ohms-per-breath with a measurement of volume-per-breath.

6. The method of claim 1, wherein detecting the change in DC trans-thoracic impedance includes determining a baseline DC trans-thoracic impedance and detecting changes in impedance from the baseline DC trans-thoracic impedance.

7. The method of claim 1, wherein adjusting the breathing volume calibration factor includes using the change in DC trans-thoracic impedance measured while the patient is in a first patient posture.

8. The method of claim 1, wherein detecting a change in DC trans-thoracic impedance includes:
   determining a first baseline DC trans-thoracic impedance for a first patient posture and a second baseline DC trans-thoracic impedance for at least a second patient posture; and
   detecting changes in impedance from the first baseline impedance when the patient is in the first posture and detecting changes in impedance from the second baseline impedance when the patient is in the second posture.

9. The method of claim 1, wherein measuring breathing volume using an implantable medical device includes monitoring breathing volume with a cardiac rhythm management device.

10. The method of claim 9, wherein the method further includes changing a pacing rate of the cardiac rhythm management device in response to the measured breathing volume.

11. The method of claim 1, wherein the method further includes storing trending information related to DC trans-thoracic impedance.

12. The method of claim 1, wherein the method further includes storing trending information related to breathing volumes.

13. The method of claim 1, wherein the method further includes communicating trending information related to one or both of the DC trans-thoracic impedance and the breathing volume to an external device for display.

14. The method of claim 1, wherein the method further includes communicating DC trans-thoracic impedance information to an external device connected to a computer network.

15. A method comprising:
   measuring a direct current (DC) component of a trans-thoracic impedance signal of a subject using an implantable medical device;
   adjusting a breathing volume calibration factor using a reference baseline value of the DC component of the trans-thoracic impedance and a measured change from the reference baseline value of the DC component of the trans-thoracic impedance, wherein the breathing volume calibration factor translates a measure of impedance to a measure of breathing volume, and the adjusted breathing volume calibration factor includes a ratio of a reference DC trans-thoracic impedance to a more recently measured value of the DC component of the trans-thoracic impedance;
   extracting a respiration signal from the trans-thoracic impedance signal, the respiration signal including the DC component of the trans-thoracic impedance that is modulated by a breathing of the subject, the respiration signal including an amplitude; and
   computing, using the implantable medical device, a breathing volume of the subject using the amplitude of the respiration signal and a breathing volume calibration factor.

16. The method of claim 15, wherein extracting the respiration signal includes filtering the trans-thoracic impedance signal to attenuate frequencies higher than 0.5 Hz.

17. The method of claim 15, wherein computing the breathing volume of the subject using the amplitude of the respiration signal includes measuring breathing volume using a peak-to-peak amplitude.

18. The method of claim 15, wherein the reference baseline value and the change from the reference baseline value are measured for a first patient posture.

19. The method of claim 15, wherein computing the breathing volume calibration factor includes computing the calibration factor using a measure of hematocrit in blood of the subject.

20. The method of claim 15, wherein computing the breathing volume calibration factor includes computing the calibration factor using a measure of resistivity of blood within a heart.

21. The method of claim 15, wherein the reference baseline value of the trans-thoracic impedance includes a DC trans-thoracic impedance value measured over a period of time.

22. The method of claim 15, wherein the calibrated breathing volume is computed by multiplying the measured breathing volume by the breathing volume calibration factor.

* * * * *